United States Patent [19]

Gordon

[11] Patent Number: 4,512,981

[45] Date of Patent: Apr. 23, 1985

[54] METHOD OF TREATING INFLAMMATION USING INOSIPLEX

[75] Inventor: Paul Gordon, Chicago, Ill.

[73] Assignee: Newport Pharmaceuticals International, Inc., Newport Beach, Calif.

[21] Appl. No.: 451,054

[22] Filed: Dec. 20, 1982

[51] Int. Cl.$^3$ .............................................. A61K 31/70
[52] U.S. Cl. ...................................... 514/45; 536/24; 514/825
[58] Field of Search ........................... 424/180; 536/24

[56] References Cited

U.S. PATENT DOCUMENTS

| | | | |
|---|---|---|---|
| 3,646,007 | 2/1972 | Gordon | 536/24 |
| 3,728,450 | 4/1973 | Gordon | 424/180 |
| 3,748,331 | 7/1973 | Cooke et al. | 260/251 |
| 3,857,940 | 12/1974 | Gordon | 424/180 |
| 4,202,895 | 5/1980 | Inaba et al. | 424/250 |
| 4,405,610 | 9/1983 | Krajevie | 424/180 |

OTHER PUBLICATIONS

Garattini et al., "International Symposium on Non-Sterodial Anti-Inflammatory Drugs", 9/8-10/1964, pp. 151-161.
Winter, "International Symposium on Non-Sterodial Anti-Inflammatory Drugs", 9/8-10/1964, pp. 190-202.
Lombardino et al., "Arzneimittel for Schung Drug Research", 1975, pp. 1629-1635.
Tew et al., "Immunology", 1980, No. 40, pp. 425-433.
Gordon et al., "International Jour. of Immunopharmacology", vol. 4, No. 4, p. 311.
Scott, Annuals of the Rheumatic Diseases, vol. 37, (1978), pp. 259-261.
Miller, Arthritis and Rheumatism, vol. 23, Feb. 1980, pp. 172-182.
Barada, Arthritis and Rheumatism, vol. 25, Jan. 1982, pp. 10-16.
Huskisson, The Lancet, Feb. 21, 1976, pp. 293-295.
Vegs, The Lancel, Apr. 10, 1976, pp. 808-809.
Vischere, The Lancet, Nov. 11, 1978, pp. 1007-1012.
Wybran, J. Rheumatology, vol. 8, Appelboom, Presentation at the 2nd International Seminar on the Treatment of Rheumatic Diseases, Israel, Nov. 24-28, 1981.
Letter of Appelboom and Wybran, May 5, 1982.
Letter of Simon to Wybran.

*Primary Examiner*—Johnnie R. Brown
*Attorney, Agent, or Firm*—Dressler, Goldsmith, Shore, Sutker & Milnamow, Ltd.

[57] ABSTRACT

Inosiplex has been found to be useful as an anti-inflammatory agent, e.g., to treat rheumatoid arthritis. There is no need to employ known anti-inflammatory agents, e.g., indomethacin or aspirin, with it and, in fact, the anti-inflammatory action of inosiplex is reduced if either of these two drugs are present.

10 Claims, 9 Drawing Figures

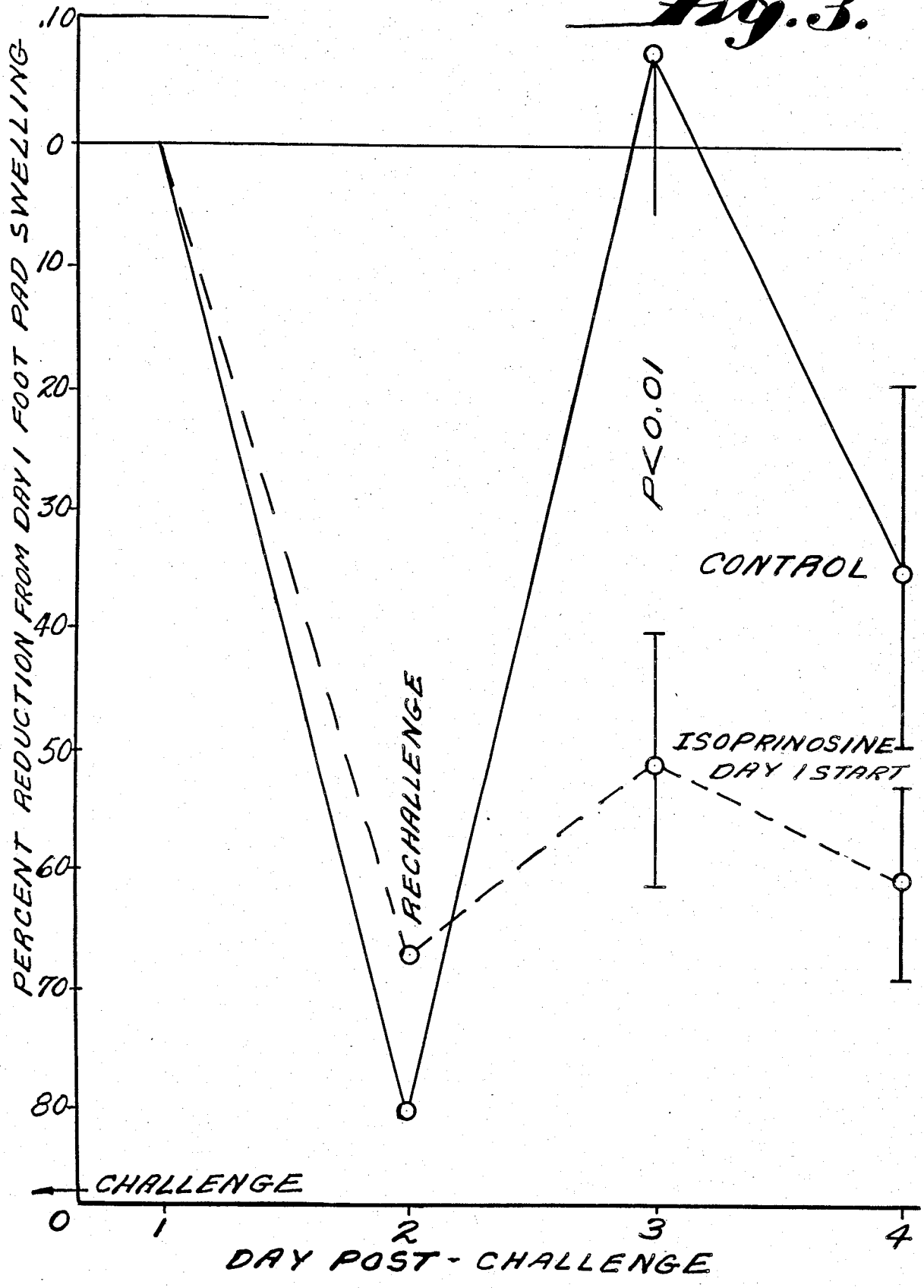

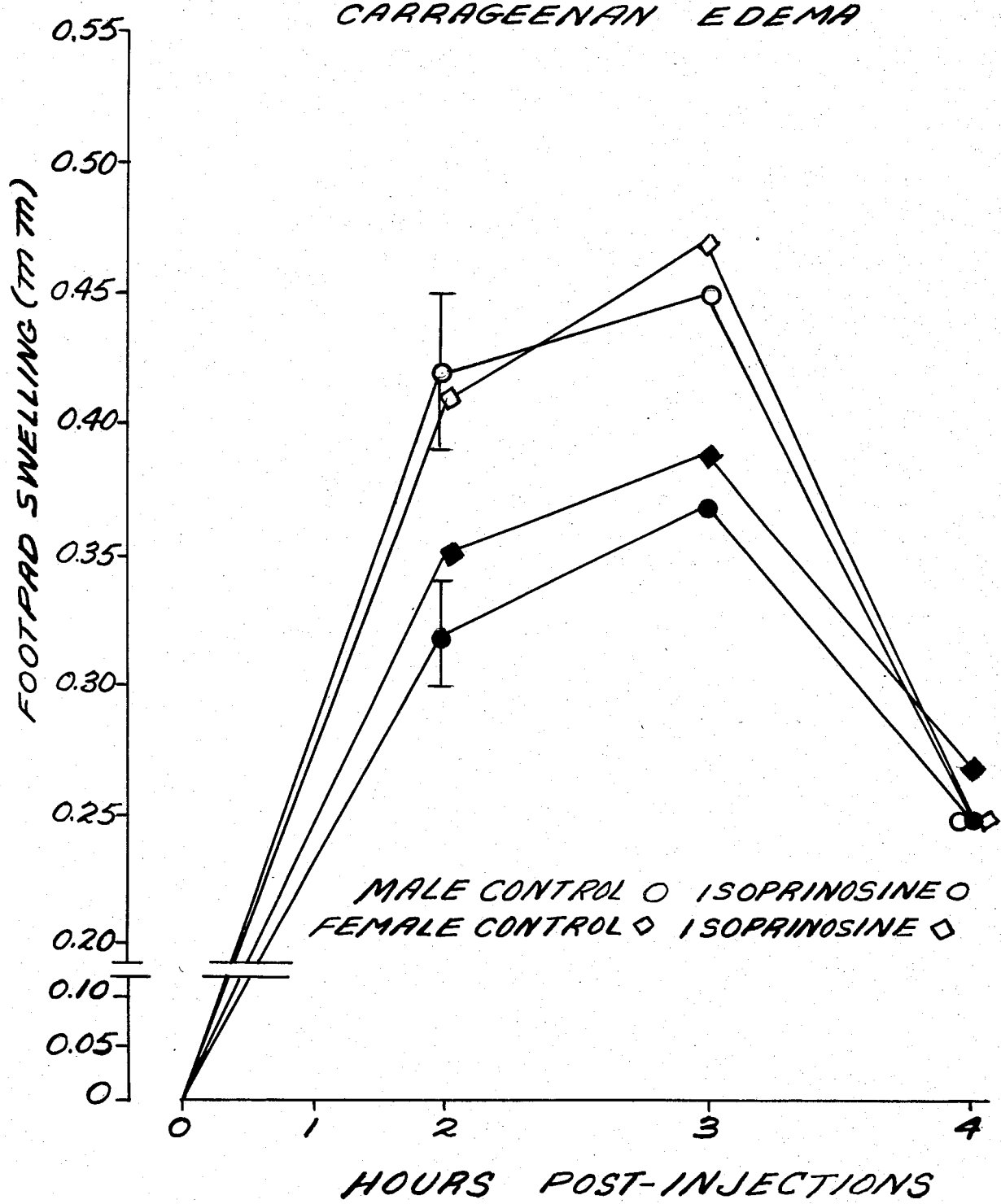

INFLAMMATION INDEX
ORAL CHALLENGE - STUDY 1

*ISO SIGNIFICANTLY LOWER THAN CONTROL AND SIGNIFICANTLY LOWER THAN INDO + ISO COMBINED. P<0.02

ORAL CHALLENGE - STUDY 2

*ISO SIGNIFICANTLY LOWER THAN ISO+SS COMBINATION P<0.02
**SS SIGNIFICANTLY LOWER THAN ISO+SS COMBINATION P<0.05

*ISO LOWER THAN CONTROL, P<0.00; ISO LOWER THAN ISO+INDO COMBINATION P<0.05
**INDO LOWER THAN CONTROL, P<0.01

*ISO LOWER THAN CONTROL, P<0.02; ISO LOWER THAN ISO+INDO COMBINATION P<0.25
**INDO LOWER THAN CONTROL, P<0.01, INDO LOWER THAN ISO+INDO COMBINATION P<0.05

METHOD OF TREATING INFLAMMATION USING INOSIPLEX

BACKGROUND OF THE INVENTION

It is known to employ levamisole, an immunomodulator as an anti-rheumatic agent, e.g., in the treatment of the inflammatory disease rheumatoid arthritis, thus see Scott, Annals of the Rheumatic Diseases, Vol. 37 (1978) pages 259–261, Miller, *Arthritis and Rheumatism,* Vol. 23, January, 1982, pages 10–16, Barada, *Arthritis and Rheumatism,* Vol. 25, January, 1982, pages 10–16, Huskison, *The Lancet,* Feb. 21, 1976, pages 393–395, Veys, *The Lancet,* Apr. 10, 1976, pages 808–809, Vischer, *The Lancet,* Nov. 11, 1978, pages 1007–1012. Levamisole in all of these studies was employed with patients maintained throughout the studies on practically fixed doses of pure anti-inflammatory drugs. Levamisole chemically is (−) 2,3,5,6-tetrahydro-6-phenylimidazo[2,1-b]thiazole.

Inosiplex is an immunomodulating agent. It is the p-acetamidobenzoic acid salt of N,N-dimethylamino-2-propanol:inosine complex 3:1 molar ratio. It is available commercially as Isoprinosine, and its manufacture and many of its uses are described in Gordon U.S. Pat. No. 3,646,007, Gordon U.S. Pat. No. 3,728,450, and Gordon U.S. Pat. No. 3,857,940. The entire disclosure of the Gordon patents is hereby incorporated by reference and relied upon.

Wybran, J. Rheumatology, Vol. 8:4, 1981, has reported that inosiplex tested favorably in treating rheumatoid arthritis. The patients were stabilized on an optimum antiinflammatory regimen which remained constant in the study. This work of Wybran and co-workers was also reported by Appelboom in a Presentation at the 2nd International Seminar on the treatment of Rheumatic Diseases in Israel Nov. 24–28, 1981. The regimen included the non-steroidal anti-inflammatory drugs indomethacin (100–150 mg) or aspirin (3 grams). This is shown in a letter of May 5, 1982, from Wybran and Appelboom to the present inventor and also a letter of Aug. 2, 1982, from Dr. Simon of Newport Pharmaceuticals International, Inc., to Dr. Wybran, which letter was acknowledged by Dr. Wybran on Aug. 9, 1982.

SUMMARY OF THE INVENTION

It has now been found that inisoplex has a broad-spectrum anti-inflammatory action, which could be useful in the treatment of rheumatoid arthritis, and that this action is not only observed in the absence of indomethacin and aspirin but is even more pronounced in the absence of such drugs.

It has been discovered that Isoprinosine can suppress the development, intensity and persistence of the delayed-type hypersensitivity response when drug administration in immunized animals is initiated after an antigen challenge. When Isoprinosine is initially administered after the antigen challenge but before the development of the delayed-type hypersensitivity response, drug treatment will suppress the development of inflammation. If, after immunization and during a series of further antigen exposures, Isoprinosine is initially administered after the onset of inflammation, treatment will suppress its intensity and persistence.

While Isoprinosine has been identified as an immunoregulatory compound acting primarily on T cell function, with regard to inflammatory processes it may also have hitherto unreported effects that are not directly concerned with immunoregulation. Isoprinosine can suppress nonspecific inflammation, such as that generated by the administration of the pro-inflammatory agent, carrageenan.

Isoprinosine has exerted both anti-allergic and nonspecific anti-inflammatory actions in model systems. The intensity of the Isoprinosine effect is similar to the effects observed for two clinically established anti-inflammatory agents: indomethacin and prednisone.

BRIEF DESCRIPTION OF THE DRAWINGS

FIG. 3 is a graph of the anti-inflammatory effect in Example 2;

FIG. 4 is a graph of the footpad swelling in Example 3;

DETAILED DESCRIPTION

EXAMPLE 1

Figure 1:
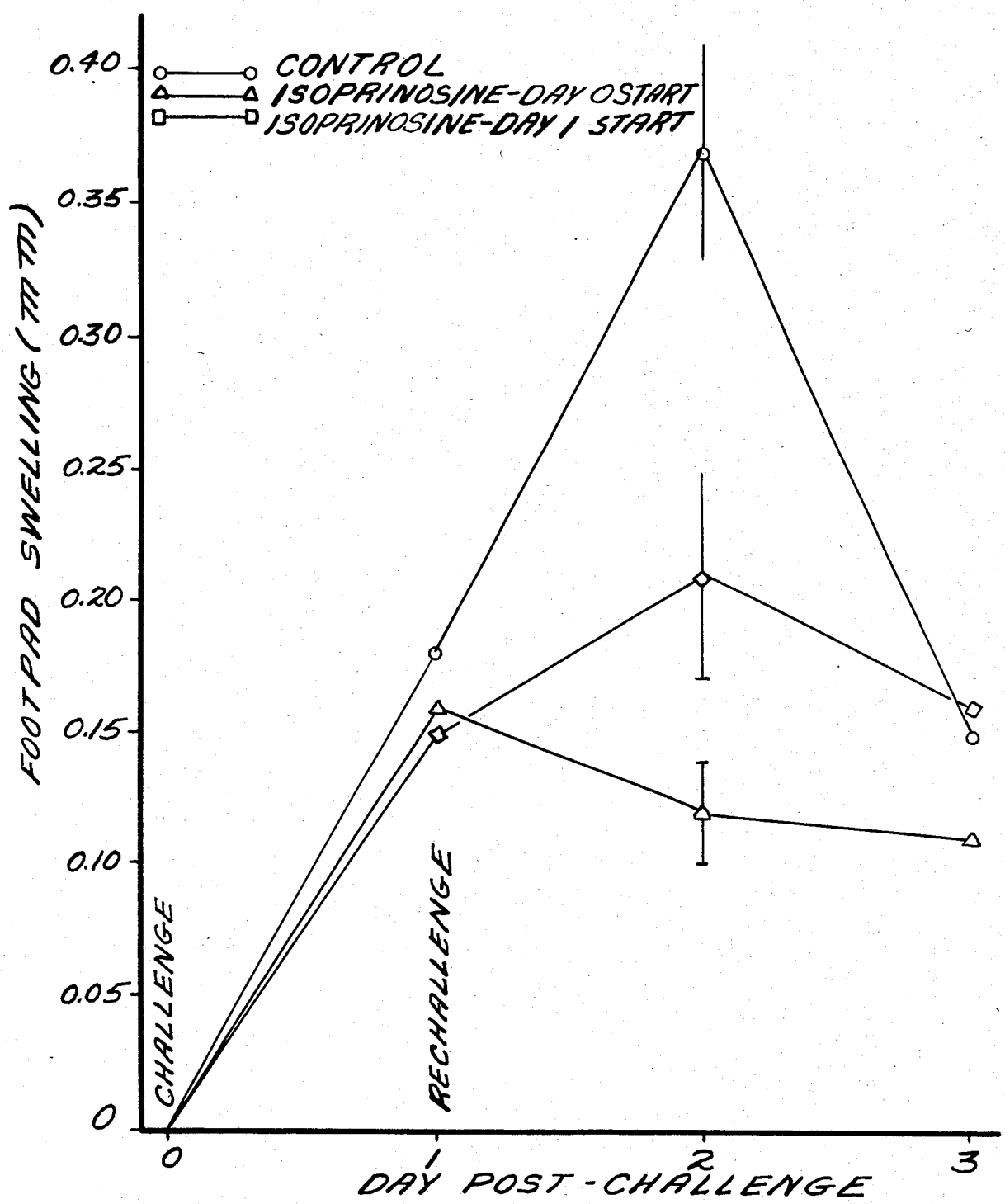
FIG. 1 is a graph of the footpad swelling in Example 1.

A STUDY OF THE EFFECTS OF ISOPRINOSINE ON FOOTPAD SWELLING IN MICE CHALLENGED ON DAY 38 AND RECHALLENGED ON DAY 39 WITH HUMAN SERUM ALBIMIN (HSA) FOLLOWING IMMUNIZATION WITH HSA IN COMPLETE FREUND'S ADJUVANT (CFA)

This is an in vivo experiment. Isoprinosine was given in the drinking water at a concentration of 0.25%.

There were employed male CD-1 mice, 5 weeks of age at time of primary immunization, obtained from Charles River.

Primary immunization—0.5 mg HSA in CFA, total volume 0.03 ml/paw, injected subcutaneously. Day 38 and day 39 challenges—1 mg HSA in normal saline by oral gavage, total volume 0.1 ml.

The methodology was essentially identical to that developed by Dr. John Tew (*Immunology* 40:425, 1980) in his studies on antigen persistence. Following initial dorsoventral paw diameter measurements by Schnelltaster caliper, 22 mice were etherized and immunized in each hind footpad with 0.03 ml of an emulsion of heat-aggregated HSA in CFA, delivering 0.5 mg HSA/paw. On day 38 (challenge day 0), the animals were randomly divided into three treatment groups, as follows:

Control (8 mice; N=16 paws).

Isoprinosine therapy initiated on Day 0 (7 mice; N=14 paws).

Isoprinosine therapy initiated on Day 1 (7 mice; N=14 paws).

Baseline footpad diameters were measured and the animals were challenged by oral gavage with 1 mg HSA in 0.1 ml normal saline. On challenge day 1 (experimental day 39), footpad measurements were taken, after which the animals were again challenged by oral gavage with 1 mg HSA in 0.1 ml normal saline. Treatments were continued through challenge day 2; footpad measurements were taken daily through challenge day 3. Paw swellings were determined using the experimental day 38 pre-challenge measurement as a baseline.

The results are given in Table 1 and FIG. 1. They establish that the development, persistence, and intensity of the delayed-type hypersensitivity response to oral antigen challenge is suppressed by treatment with Isoprinosine, when administered immediately after or one day following antigen challenge.

Histopathologic analysis of the cell types contributing to the inflammatory exudate have revealed these to be exclusively mononuclear cells, largely monocytic; occasional foci of lymphocyte clusters were also found.

The results of the drug study indicate that Isoprinosine can be useful in the treatment of delayed-type hypersensitivity responses in parts of the body that antigen or antigen fragments reach via the bloodstream (as well as by other routes). Such disease states could include rheumatoid arthritis and a variety of allergic and dermatologic disorders.

Day 59 and Day 61 challenges—$3 \times 10^4$ E. coli in saline injected subcutaneously in the footpad, total volume 0.03 ml.

The methodology was essentially identical to that developed by Dr. John Tew (Immunology 40:425, 1980). Following initial dorsoventral paw diameter measurements by Schnelltaster caliper, 23 mice were etherized and immunized in each hind footpad with 0.03 ml containing $3 \times 10^4$ heat-killed E. coli in CFA. On day 59 (challenge day 0), the mice were measured for baseline paw diameter, etherized and challenged in both hind footpads with 0.03 ml containing $3 \times 10^4$ heat-killed E. coli in saline; this same procedure was repeated on day 61 (challenge day 2). Treatments were as follows:

Control (8 mice; N=16 paws).
Isoprinosine initiated on Day 0 (8 mice; N=16 paws).
Isoprinosine initiated on Day 1 (7 mice; N=14 paws).

The following "blank" were "immunized" and "challenged" according to the same schedule as the experimental animals; these "blank" groups, like the Controls, received only plain drinking water.

TABLE 1

| | Footpad Swelling (mm) | | | | | | | | | |
|---|---|---|---|---|---|---|---|---|---|---|
| | Day 1 | | Day 2 | | Day 3 | | Sum Days 1-3 | | Sum Days 2&3 | |
| | L | R | L | R | L | R | L | R | L | R |
| Control 1 | 0.1 | 0.2 | 0.4 | 0.4 | 0.2 | 0.1 | 0.7 | 0.7 | 0.6 | 0.5 |
| 2 | 0.1 | 0.2 | 0.3 | 0.2 | 0.1 | 0.2 | 0.5 | 0.6 | 0.4 | 0.4 |
| 3 | 0.3 | 0.3 | 0.4 | 0.5 | 0.1 | 0.1 | 0.8 | 0.9 | 0.5 | 0.6 |
| 4 | 0.2 | 0.1 | 0.2 | 0.1 | 0.1 | −0.1 | 0.5 | 0.1 | 0.3 | 0.0 |
| 5 | 0.2 | 0.3 | 0.5 | 0.6 | 0.2 | 0.3 | 0.9 | 1.2 | 0.7 | 0.9 |
| 6 | 0.1 | 0.2 | 0.5 | 0.4 | 0.3 | 0.3 | 0.9 | 0.9 | 0.8 | 0.7 |
| 7 | 0.1 | 0.1 | 0.4 | 0.5 | 0.1 | 0.1 | 0.6 | 0.7 | 0.5 | 0.6 |
| 8 | 0.2 | 0.2 | 0.3 | 0.2 | 0.2 | 0.1 | 0.7 | 0.5 | 0.5 | 0.3 |
| Average ± SE = | 0.18 | ± 0.02 | 0.37 | ± 0.04 | 0.15 | ± 0.03 | 0.70 | ± 0.06 | 0.52 | ± 0.05 |
| Isoprinosine 1 | 0.4 | 0.0 | 0.1 | 0.0 | 0.2 | −0.1 | 0.7 | −0.1 | — | |
| Day 0 Start 2 | 0.1 | 0.3 | 0.1 | 0.2 | 0.1 | 0.2 | 0.3 | 0.7 | — | |
| 3 | 0.2 | 0.1 | 0.2 | 0.0 | 0.2 | 0.1 | 0.6 | 0.2 | — | |
| 4 | 0.2 | 0.2 | 0.2 | 0.3 | 0.2 | 0.2 | 0.6 | 0.7 | — | |
| 5 | 0.2 | 0.1 | 0.0 | 0.1 | 0.1 | 0.1 | 0.3 | 0.3 | — | |
| 6 | 0.2 | 0.3 | 0.1 | 0.1 | 0.1 | 0.1 | 0.4 | 0.5 | — | |
| 7 | 0.0 | 0.0 | 0.2 | 0.1 | 0.1 | 0.0 | 0.3 | 0.1 | — | |
| Average ± SE = | 0.16 | ± 0.03 | 0.12 | ± 0.02 | 0.11 | ± 0.02 | 0.40 | ± 0.07 | | |
| by t Test | NS | | $P < 0.001$ | | NS | | $P < 0.01$ | | | |
| Isoprinosine 1 | 0.1 | 0.2 | 0.3 | 0.3 | 0.1 | 0.1 | — | | 0.4 | 0.4 |
| Day 1 Start 2 | 0.2 | 0.4 | 0.2 | 0.3 | 0.1 | 0.3 | — | | 0.3 | 0.6 |
| 3 | 0.2 | 0.3 | 0.4 | 0.4 | 0.4 | 0.3 | — | | 0.8 | 0.7 |
| 4 | 0.0 | 0.1 | 0.2 | 0.1 | 0.2 | 0.1 | — | | 0.4 | 0.2 |
| 5 | 0.0 | 0.2 | 0.2 | 0.4 | 0.0 | 0.2 | — | | 0.2 | 0.6 |
| 6 | 0.0 | 0.1 | 0.1 | 0.2 | 0.2 | 0.2 | — | | 0.3 | 0.4 |
| 7 | 0.1 | 0.2 | −0.1 | 0.0 | 0.0 | 0.0 | — | | −0.1 | 0.0 |
| Average ± SE = | 0.15 | ± 0.03 | 0.21 | ± 0.04 | 0.16 | ± 0.03 | | | 0.37 | ± 0.07 |
| by t Test | NS | | $P < 0.01$ | | NS | | | | NS | |

EXAMPLE 2

A STUDY OF THE EFFECTS OF ISOPRINOSINE ON FOODPAD SWELLING IN MICE CHALLENGED ON DAY 59 AND RECHALLENGED ON DAY 61 WITH E. COLI IN SALINE FOLLOWING IMMUNIZATION WITH E. COLI IN COMPLETE FREUND'S ADJUVANT (CFA)

This is an in vivo experiment. Isoprinosine was given in the drinking water at a concentration of 0.25%.

There were employed male CD-1 mice, 4 weeks of age at the time of primary immunization, obtained from Charles River.

Primary immunization—$3 \times 10^4$ E. coli in CFA injected subcutaneously in the footpad, total volume 0.03 ml.

Immunization—Saline; Challenge—Saline (6 mice; N=12 paws).

Immunization—CFA; Challenge—Saline (6 mice; N=12 paws).

Immunization—E. coli in Saline; Challenge—E. coli (5 mice; N=10 paws).

Immunization—CFA; Challenge—E. coli (6 mice; N=12 paws).

Treatments were continued through challenge day 4; footpad measurements were taken daily through day 4 and paw swellings were determined.

Figure 2:
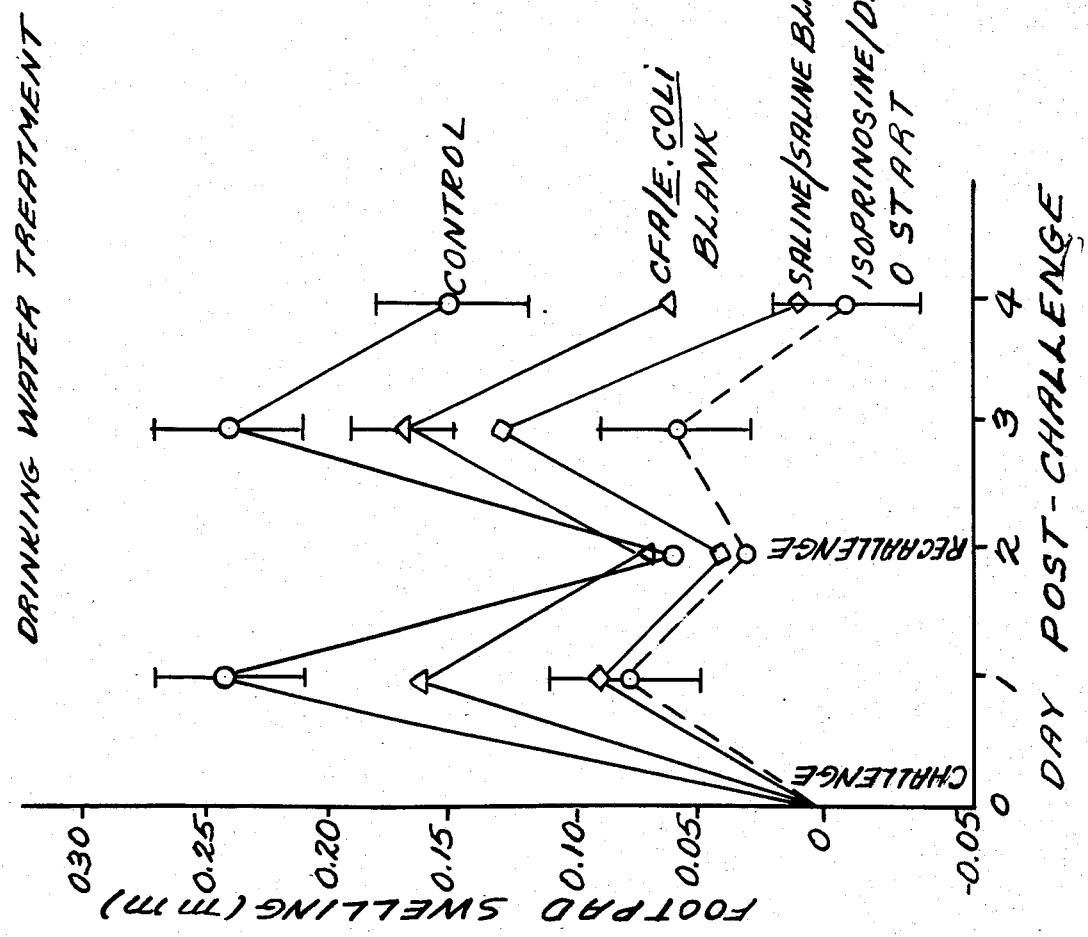
FIG. 2 is a graph of the footpad swelling in Example 2.
Figure 6:
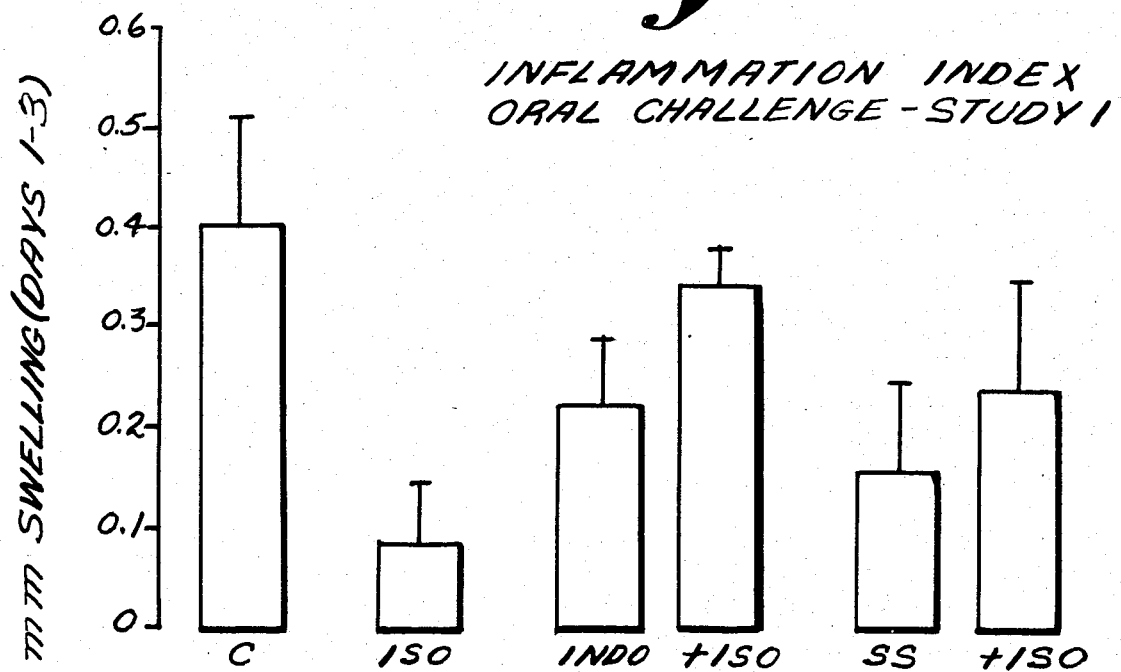
FIGS. 6, 7, 8, and 9 are block charts of comparisions of footpad swelling with controls, Isoprinosine, indomethacin, indomethacin with Isoprinosine, sodium salicylate, and sodium salicylate with Isoprinosine described in Example 8.
Figure 7:
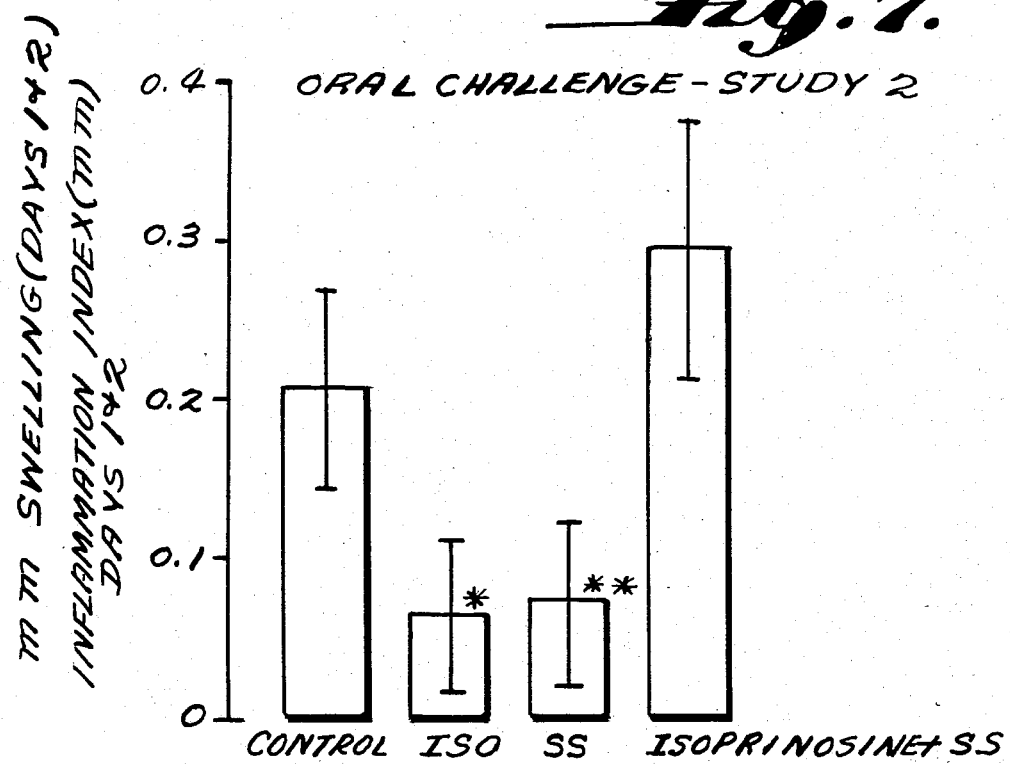
Figure 8:
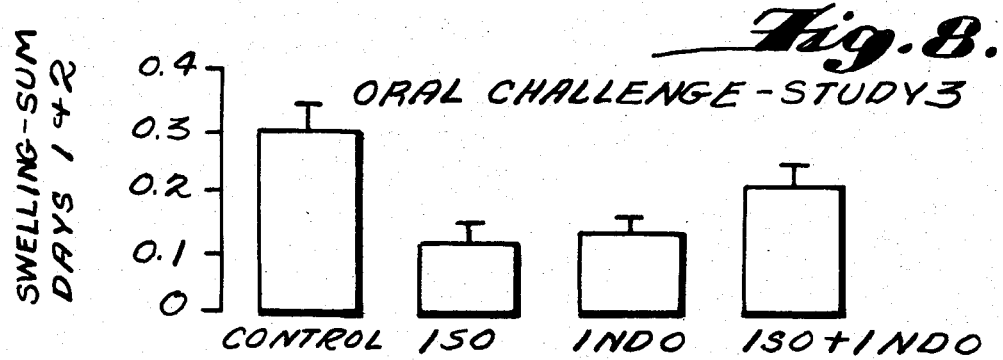
Figure 9:
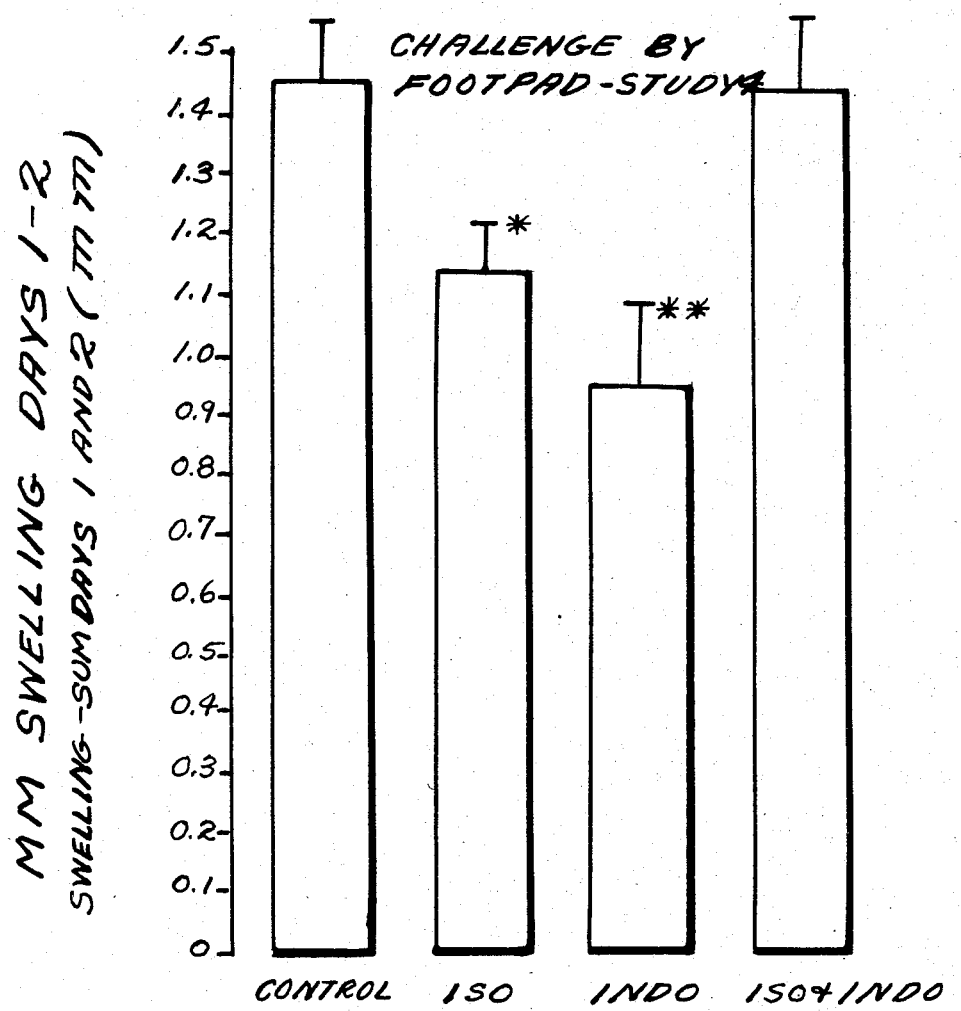

The results identify two peaks, each of which developed one day following a footpad challenge (challenges on days 0 and 2; peaks on days 1 and 3). When treatment with Isoprinosine was initiated on day 0 immediately following the initial challenge with E. coli in saline, the degree of inflammation is seen to be even less than that resulting from the injection of the saline/saline and other blanks (see Table 3 and FIG. 2), suggesting a non-specific anti-inflammatory effect, as well as a specific anti-allergic anti-inflammatory effect. When Isoprinosine treatment is initiated on day 1, following the onset of inflammation, Isoprinosine is found to exert a significant anti-inflammatory effect as well (see Table 2 and FIG. 3).

In this model, administration of antigen is local (subcutaneous injection in the footpad) and is in relatively high concentrations, in contrast to the study (Example 1) employing the orally administered challenge with HSA (human serum albumin). The high local concentration of antigen may be associated with the generation by macrophages of suppressor prostaglandin secretion (PGE). It is of interest that, in Table 4 (a summary of certain other drug studies), indomethacin is found to suppress the paw inflammation generated by oral HSA but not that generated by paw-injected $E.\ coli$. Since indomethacin is a prostaglandin synthesis inhibitor, it may be assumed that its absence of effect on the $E.\ coli$ model results from the different pattern of prostaglandins produced. Specifically, in this model the immunosuppressor actions of macrophage-derived $PGE_1$ may have become so significant an output within the immuno-regulatory network that the administration of indomethacin, by depressing the generation of this immunosuppressive regulator as well as other proinflammatory prostaglandins, may exert a null net effect.

The importance of this observation is that Isoprinosine can specifically be effectively anti-inflammatory when indomethacin is not. Since it is known that about 30–40% of all rheumatoid arthritics do not respond to compounds of the indomethacin type, such indomethacin-resistant population can be targeted for treatment with Isoprinosine.

The results of this study also suggest the value of using Isoprinosine in the treatment of a panoply of human dermatologic, allergic, and gastrointestinal disorders that are expressions of hypersensitivity states.

TABLE 2

| | | Footpad Swelling (mm) | | | | | | | | | | |
|---|---|---|---|---|---|---|---|---|---|---|---|---|
| | | Day 1 | | Day 2 | | Day 3 | | Day 4 | | Sum Days 1–4 | | Sum Days 3&4 | |
| | | L | R | L | R | L | R | L | R | L | R | L | R |
| Control | 1 | 0.2 | 0.3 | 0.1 | 0.0 | 0.3 | 0.3 | 0.3 | 0.3 | 0.9 | 0.9 | 0.6 | 0.6 |
| | 2 | 0.3 | 0.5 | 0.1 | 0.1 | 0.2 | 0.4 | 0.2 | 0.3 | 0.8 | 1.3 | 0.4 | 0.7 |
| | 3 | 0.4 | 0.2 | 0.2 | 0.0 | 0.4 | 0.2 | 0.4 | −0.1 | 1.4 | 0.3 | 0.8 | 0.1 |
| | 4 | 0.1 | 0.3 | −0.1 | 0.1 | 0.2 | 0.2 | 0.0 | 0.1 | 0.2 | 0.7 | 0.2 | 0.3 |
| | 5 | 0.2 | 0.2 | 0.2 | 0.1 | 0.3 | 0.2 | 0.1 | 0.1 | 0.8 | 0.6 | 0.4 | 0.3 |
| | 6 | 0.2 | 0.1 | 0.0 | 0.1 | 0.2 | 0.2 | 0.1 | 0.2 | 0.5 | 0.6 | 0.3 | 0.4 |
| | 7 | 0.1 | 0.2 | 0.0 | −0.1 | 0.0 | 0.2 | 0.1 | 0.2 | 0.2 | 0.5 | 0.1 | 0.4 |
| | 8 | 0.3 | 0.3 | 0.0 | 0.1 | 0.3 | 0.3 | 0.0 | 0.1 | 0.6 | 0.8 | 0.3 | 0.4 |
| Average ± SE = | | 0.24 | ± 0.03 | 0.06 | ± 0.02 | 0.24 | ± 0.02 | 0.15 | ± 0.03 | 0.69 | ± 0.08 | 0.39 | ± 0.05 |
| Isoprinosine | 1 | 0.0 | 0.1 | −0.1 | 0.1 | −0.2 | 0.2 | −0.1 | 0.0 | −0.4 | 0.4 | — | |
| Day 0 Start | 2 | 0.2 | 0.0 | 0.0 | 0.0 | 0.2 | 0.2 | 0.2 | −0.1 | 0.6 | 0.1 | — | |
| | 3 | 0.1 | 0.3 | 0.0 | 0.0 | 0.1 | 0.0 | 0.0 | 0.0 | 0.2 | 0.3 | — | |
| | 4 | 0.1 | 0.1 | 0.1 | 0.2 | −0.1 | 0.0 | −0.2 | 0.0 | −0.1 | 0.3 | — | |
| | 5 | 0.0 | 0.0 | 0.2 | 0.0 | 0.1 | −0.1 | 0.0 | 0.0 | 0.3 | −0.1 | — | |
| | 6 | 0.0 | 0.2 | −0.1 | 0.0 | 0.1 | 0.2 | 0.0 | 0.2 | 0.0 | 0.6 | — | |
| | 7 | −0.1 | −0.1 | 0.0 | 0.0 | 0.0 | 0.0 | 0.0 | 0.0 | −0.1 | −0.01 | — | |
| | 8 | 0.2 | 0.2 | 0.1 | 0.0 | 0.2 | 0.0 | 0.1 | −0.2 | 0.6 | 0.0 | — | |
| Average ± SE = | | 0.08 | ± 0.03 | 0.03 | ± 0.02 | 0.06 | ± 0.03 | −0.01 | ± 0.03 | 0.16 | ± 0.07 | | |
| by t Test = | | P < 0.001 | | NS | | P < 0.001 | | P < 0.01 | | P < 0.001 | | | |
| Isoprinosine | 1 | 0.3 | 0.3 | 0.0 | 0.1 | 0.2 | 0.2 | 0.2 | 0.2 | — | | 0.4 | 0.4 |
| Day 1 Start | 2 | 0.2 | 0.3 | 0.1 | 0.2 | 0.1 | 0.1 | 0.1 | 0.1 | — | | 0.2 | 0.2 |
| | 3 | 0.3 | 0.4 | 0.0 | 0.0 | −0.1 | 0.1 | 0.0 | −0.1 | — | | −0.1 | 0.0 |
| | 4 | 0.2 | 0.3 | 0.0 | 0.1 | 0.1 | 0.3 | 0.1 | 0.2 | — | | 0.2 | 0.5 |
| | 5 | 0.3 | 0.3 | 0.0 | 0.2 | 0.3 | 0.3 | 0.1 | 0.2 | — | | 0.4 | 0.5 |
| | 6 | 0.2 | 0.3 | 0.2 | 0.0 | 0.0 | 0.2 | 0.0 | 0.1 | — | | 0.0 | 0.3 |
| | 7 | 0.4 | 0.5 | 0.3 | 0.2 | 0.0 | 0.3 | 0.2 | 0.3 | — | | 0.2 | 0.6 |
| Average ± SE = | | 0.31 | ± 0.02 | 0.10 | ±0.03 | 0.15 | ±0.03 | 0.12 | ± 0.03 | | | 0.27 | ± 0.06 |
| by t Test = | | | | NS | | P < 0.05 | | NS | | | | NS | |

TABLE 3

| | | Blanks | | | | | | | | | |
|---|---|---|---|---|---|---|---|---|---|---|---|
| | | Footpad Swelling (mm) | | | | | | | | | |
| | | Day 1 | | Day 2 | | Day 3 | | Day 4 | | 4-Day Total | |
| | | L | R | L | R | L | R | L | R | L | R |
| Immunize | 1 | 0.2 | 0.1 | 0.0 | 0.1 | 0.1 | 0.2 | 0.0 | 0.0 | 0.3 | 0.4 |
| Saline | 2 | 0.2 | 0.2 | 0.1 | 0.1 | 0.1 | 0.2 | 0.0 | 0.1 | 0.4 | 0.6 |
| Challenge | 3 | −0.1 | 0.0 | 0.0 | 0.0 | −0.1 | 0.0 | −0.1 | −0.1 | −0.3 | −0.1 |
| Saline | 4 | 0.0 | 0.1 | 0.1 | 0.0 | 0.0 | 0.2 | 0.1 | 0.1 | 0.0 | 0.4 |
| | 5 | 0.1 | 0.1 | 0.0 | 0.0 | 0.3 | 0.2 | 0.0 | 0.1 | 0.4 | 0.4 |
| | 6 | 0.1 | 0.1 | 0.1 | 0.0 | 0.2 | 0.1 | 0.1 | 0.0 | 0.5 | 0.2 |
| Average ± SD | | 0.09 | ± 0.09 | 0.04 | ± 0.05 | 0.13 | ± 0.11 | 0.01 | ± 0.08 | 0.27 | ± 0.27 |
| Immunize | 1 | 0.0 | 0.1 | 0.0 | 0.0 | 0.0 | 0.1 | 0.1 | 0.1 | 0.1 | 0.3 |
| CFA | 2 | 0.0 | 0.0 | 0.0 | 0.1 | 0.2 | 0.1 | 0.0 | 0.0 | 0.2 | 0.2 |
| Challenge | 3 | 0.1 | 0.1 | 0.0 | 0.0 | 0.2 | 0.1 | 0.0 | 0.0 | 0.3 | 0.2 |
| Saline | 4 | 0.1 | 0.1 | 0.0 | 0.0 | 0.0 | 0.0 | 0.1 | 0.0 | 0.2 | 0.0 |
| | 5 | 0.2 | 0.1 | 0.0 | 0.1 | 0.2 | 0.1 | 0.1 | 0.1 | 0.5 | 0.4 |
| | 6 | 0.1 | 0.1 | 0.0 | 0.1 | 0.0 | 0.2 | 0.0 | 0.1 | 0.1 | 0.5 |
| Average ± SD | | 0.08 | ± 0.06 | 0.03 | ± 0.05 | 0.10 | ± 0.09 | 0.05 | ± 0.05 | 0.25 | ± 0.16 |
| Immunize | 1 | 0.1 | 0.1 | 0.0 | 0.0 | 0.2 | 0.2 | 0.0 | 0.1 | 0.3 | 0.4 |

TABLE 3-continued

| | | Blanks Footpad Swelling (mm) | | | | | | | | | |
|---|---|---|---|---|---|---|---|---|---|---|---|
| | | Day 1 | | Day 2 | | Day 3 | | Day 4 | | 4-Day Total | |
| | | L | R | L | R | L | R | L | R | L | R |
| E. coli | 2 | 0.1 | 0.2 | 0.1 | 0.0 | 0.3 | 0.2 | 0.1 | 0.1 | 0.6 | 0.5 |
| in saline | 3 | 0.2 | 0.1 | 0.0 | 0.0 | 0.2 | 0.1 | 0.1 | 0.0 | 0.5 | 0.2 |
| Challenge | 4 | 0.2 | −0.1 | 0.1 | 0.1 | 0.2 | 0.2 | 0.2 | 0.0 | 0.7 | 0.2 |
| E. coli | 5 | 0.1 | 0.0 | 0.1 | 0.0 | 0.0 | 0.3 | 0.1 | 0.1 | 0.5 | 0.4 |
| Average ± SD | | 0.10 ± 0.09 | | 0.04 ± 0.05 | | 0.21 ± 0.06 | | 0.08 ± 0.06 | | 0.43 ± 0.16 | |
| Immunize | 1 | 0.2 | 0.1 | 0.0 | 0.2 | 0.2 | 0.1 | 0.1 | 0.2 | 0.5 | 0.6 |
| CFA | 2 | 0.1 | 0.2 | 0.0 | 0.0 | 0.1 | 0.1 | 0.0 | 0.0 | 0.2 | 0.3 |
| Challenge | 3 | 0.0 | 0.2 | 0.1 | 0.1 | 0.2 | 0.3 | 0.1 | 0.1 | 0.4 | 0.7 |
| E. coli | 4 | 0.1 | 0.1 | 0.1 | 0.0 | 0.3 | 0.1 | 0.1 | −0.1 | 0.6 | 0.1 |
| | 5 | 0.2 | 0.1 | 0.2 | 0.0 | 0.2 | 0.1 | 0.1 | 0.1 | 0.7 | 0.3 |
| | 6 | 0.3 | 0.3 | 0.1 | 0.0 | 0.1 | 0.2 | 0.0 | 0.0 | 0.5 | 0.5 |
| Average ± SD | | 0.16 ± 0.09 | | 0.07 ± 0.08 | | 0.17 ± 0.08 | | 0.06 ± 0.08 | | 0.45 ± 0.19 | |

TABLE 4

Significant Inflammation Suppression in Delayed-Type Hypersensitivity

| | Antigen Challenge Model | |
|---|---|---|
| Therapy | Low Antigen/Oral HSA | High Antigen/Local E. coli |
| Isoprinosine | Yes | Yes |
| Cytoxan | Yes | Yes |
| Indomethacin | Yes | No |
| Prednison | Yes | — |
| Levamisole | Yes | Yes |

EXAMPLE 3

A STUDY OF THE EFFECT OF ISOPRINOSINE ON FOOTPAD SWELLING OF MICE FOLLOWING THE INJECTION OF CARREGEENAN

This is an in vivo experiment. Isoprinosine was given at 500 mg/kg by oral gavage 2 hours prior to carrageenan injection, total volume 0.1 ml.

There were employed male and female CD-1 mice, 6 weeks of age, born in house.

The inoculum was 80 μg/paw lambda carrageenan, type IV (Sigma Chemical Co. Lot #40F-0388), made up in saline, total volume 0.03 ml.

Two hours prior to carrageenan injection, the mice received oral gavage of 0.1 ml distilled water or water containing 500 mg/kg Isoprinosine. Two hours later, following initial footpad measurements using a Schnell-taster caliper, 11 male and 10 female mice were etherized and injected subcutaneously in each hind footpad with 80 μg carrageenan. Footpad measurements were taken at 2, 3, and 4 hours post-carrageenan injection, and paw swellings were determined.

The results of this first experiment of Isoprinosine effects on carrageenan edema, shown in Tables 5 and 6 and FIG. 4, establish that Isoprinosine exerts a significant anti-inflammatory effect more marked in male than in female mice.

The mice used in this study were exceptionally hyperactive, indicating an endogenous stress state. In a probably related finding, the 3-hour control peak was about half of what was observed in most previous carrageenan studies. Characteristically, it was found that the anti-inflammatory effects were more pronounced when the control peak reaches the typical elevation. Nevertheless, the acute anti-inflammatory effects observed for Isoprinosine are significant and, at 2 hours, are similar to the acute anti-inflammatory effects observed for 5 mg/kg indomethacin (Isoprinosine, 24% reduction in footpad swelling; indomethacin, 36%).

TABLE 5

| | | Male Mice | | | | | |
|---|---|---|---|---|---|---|---|
| | | Footpad Swelling (mm) | | | | | |
| | | 2 Hours | | 3 Hours | | 4 Hours | |
| | | L | R | L | R | L | R |
| Control | 1 | 0.3 | 0.3 | 0.2 | 0.4 | 0.1 | 0.2 |
| | 2 | 0.3 | 0.4 | 0.4 | 0.3 | 0.2 | 0.1 |
| | 3 | 0.5 | 0.4 | 0.4 | 0.5 | 0.4 | 0.4 |
| | 4 | 0.5 | 0.4 | 0.5 | 0.5 | 0.1 | 0.2 |
| | 5 | 0.5 | 0.6 | 0.6 | 0.7 | 0.3 | 0.5 |
| Average ± SE | | 0.42 ± 0.03 | | 0.45 ± 0.05 | | 0.25 ± 0.05 | |
| Isoprinosine | 1 | 0.5 | 0.4 | 0.6 | 0.6 | 0.4 | 0.3 |
| | 2 | 0.3 | 0.3 | 0.3 | 0.4 | 0.2 | 0.3 |
| | 3 | 0.3 | 0.2 | 0.2 | 0.3 | 0.2 | 0.2 |
| | 4 | 0.2 | 0.3 | 0.4 | 0.3 | 0.1 | 0.3 |
| | 5 | 0.3 | 0.3 | 0.2 | 0.3 | 0.2 | 0.3 |
| | 6 | 0.4 | 0.3 | 0.4 | 0.4 | 0.3 | 0.2 |
| Average ± SE by t Test | | 0.32 ± 0.02 P < 0.02 | | 0.37 ± 0.04 NS | | 0.25 ± 0.02 NS | |

TABLE 6

| | | Female Mice | | | | | |
|---|---|---|---|---|---|---|---|
| | | Footpad Swelling (mm) | | | | | |
| | | 2 Hours | | 3 Hours | | 4 Hours | |
| | | L | R | L | R | L | R |
| Control | 1 | 0.4 | 0.3 | 0.4 | 0.3 | 0.3 | 0.2 |
| | 2 | 0.5 | 0.5 | 0.4 | 0.5 | 0.2 | 0.2 |
| | 3 | 0.5 | 0.5 | 0.8 | 0.7 | 0.4 | 0.4 |
| | 4 | 0.3 | 0.2 | 0.5 | 0.2 | 0.1 | 0.1 |
| | 5 | 0.5 | 0.4 | 0.5 | 0.4 | 0.3 | 0.3 |
| Average ± SE | | 0.41 ± 0.03 | | 0.47 ± 0.06 | | 0.25 ± 0.03 | |
| Isoprinosine | 1 | 0.4 | 0.5 | 0.6 | 0.5 | 0.4 | 0.4 |
| | 2 | 0.2 | 0.2 | 0.3 | 0.3 | 0.3 | 0.1 |
| | 3 | 0.4 | 0.3 | 0.4 | 0.3 | 0.3 | 0.2 |
| | 4 | 0.6 | 0.3 | 0.6 | 0.3 | 0.3 | 0.1 |
| | 5 | 0.2 | 0.4 | 0.2 | 0.4 | 0.2 | 0.4 |
| Average ± SE by t Test | | 0.35 ± 0.04 NS | | 0.39 ± 0.04 NS | | 0.27 ± 0.04 NS | |

EXAMPLE 4

FURTHER STUDY OF THE EFFECT OF ISOPRINOSINE ON FOOTPAD SWELLING OF MICE FOLLOWING THE INJECTION OF CARRAGEENAN

This is an in vivo experiment. Isoprinosine was given at 100 and 500 mg/kg by oral gavage 2 hours prior to carrageenan injection, total volume 0.1 ml.

There were employed male CD-1 mice, 4 weeks of age, obtained from Charles River.

The inoculum was 80 μg/paw lambda carrageenan, type IV (Sigma Chemical Company Lot 190 40F-0388), made up in saline, total volume 0.03 ml.

Two hours prior to carrageenan injection, 24 mice were given an oral gavage of 0.1 ml of distilled water or water containing 100 or 500 mg/kg Isoprinosine. Two hours later, following initial dorsoventral paw diameter measurements using a Schnelltaster caliper, the mice were etherized and injected subcutaneously in each hind footpad with 80 μg carrageenan. Footpad measurements were taken hourly for 4 hours post-carrageenan injection, and paw swellings were determined.

Figure 5:
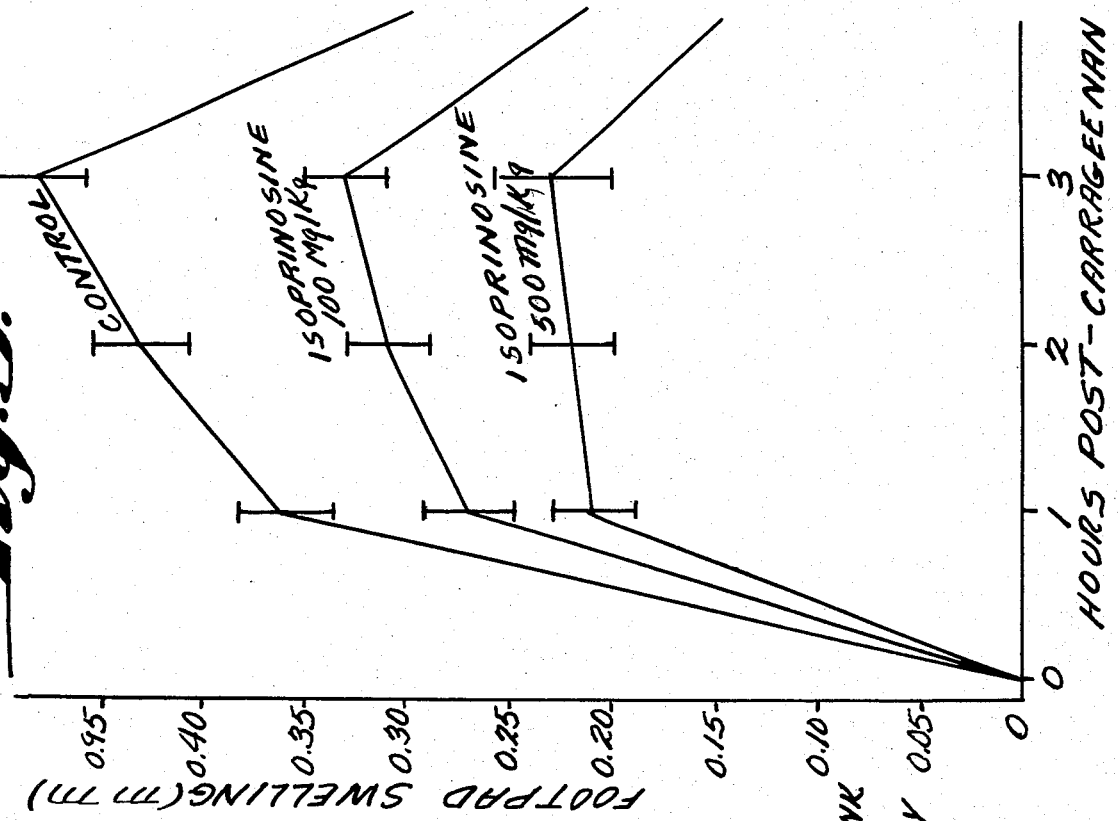
FIG. 5 is a graph of the footpad swelling in Example 4.

The results, shown in Table 7 and FIG. 5, confirm that Isoprinosine suppresses carrageenan-induced footpad swelling. Both the 100 and the 500 mg/kg doses exerted very significant anti-inflammatory effects.

A two-point dose response curve can be generated from the data.

The Isoprinosine anti-inflammatory effects that were generated in this study are more profound than in Example 1, and are somewhat more pronounced than typically observed for 5 mg/kg indomethacin.

geenan model, Levamisole does not. This difference is in contrast to the observations found by applicant for in vivo antigen-specific immunological inflammation and the observations made by Hadden (*Int. J. Immunopharmac.* 1:17–27, 1979) on in vitro immune parameters, especially lymphokine action and PHA-induced lymphocyte proliferation, where both drugs had similar effects.

The effect of Isoprinosine on non-specific inflammation, as demonstrated in the carrageenan model indicates broader anti-inflammatory uses for Isoprinosine than for Levamisole, and to predict an earlier onset of anti-inflammatory effects than that observed for Levamisole in the treatment of rheumatoid arthritis, wherein both immunological and non-immunological components of inflammation are operative.

|  | Footpad Swelling (mm) at 3-hr Post-Carrageenan | % Drug Effect |
|---|---|---|
| Control | 0.53 ± 0.04 | |
| Isoprinosine 100 mg/kg | 0.30 ± 0.03* | 43% |
| Isoprinosine 500 mg/kg | 0.32 ± 0.04* | 40% |
| Levamisole 2.5 mg/kg | 0.48 ± 0.04 | 9% |
| Levamisole 25 mg/kg | 0.52 ± 0.03 | 2% |

*P < 0.001

TABLE 7

| | Carrageenan Footpad Swelling (mm) | | | | | | | |
|---|---|---|---|---|---|---|---|---|
| | 1 Hour | | 2 Hours | | 3 Hours | | 4 Hours | |
| | L | R | L | R | L | R | L | R |
| Control 1 | 0.4 | 0.5 | 0.4 | 0.5 | 0.5 | 0.5 | 0.3 | 0.4 |
| 2 | 0.3 | 0.3 | 0.4 | 0.4 | 0.5 | 0.5 | 0.3 | 0.3 |
| 3 | 0.4 | 0.4 | 0.3 | 0.6 | 0.4 | 0.4 | 0.2 | 0.3 |
| 4 | 0.4 | 0.4 | 0.5 | 0.5 | 0.5 | 0.5 | 0.3 | 0.2 |
| 5 | 0.3 | 0.2 | 0.4 | 0.4 | 0.5 | 0.6 | 0.3 | 0.3 |
| 6 | 0.2 | 0.3 | 0.3 | 0.4 | 0.4 | 0.5 | 0.1 | 0.3 |
| 7 | 0.3 | 0.4 | 0.3 | 0.5 | 0.4 | 0.6 | 0.3 | 0.5 |
| 8 | 0.4 | 0.5 | 0.5 | 0.5 | 0.4 | 0.4 | 0.3 | 0.3 |
| Average ± SE = | 0.36 ± 0.02 | | 0.43 ± 0.02 | | 0.48 ± 0.02 | | 0.29 ± 0.02 | |
| Isoprinosine 1 | 0.3 | 0.4 | 0.4 | 0.3 | 0.4 | 0.5 | 0.2 | 0.3 |
| 100 mg/kg 2 | 0.2 | 0.2 | 0.3 | 0.3 | 0.3 | 0.3 | 0.2 | 0.2 |
| 3 | 0.3 | 0.2 | 0.2 | 0.3 | 0.3 | 0.4 | 0.2 | 0.2 |
| 4 | 0.3 | 0.4 | 0.3 | 0.3 | 0.3 | 0.4 | 0.3 | 0.3 |
| 5 | 0.3 | 0.4 | 0.3 | 0.4 | 0.2 | 0.3 | 0.2 | 0.1 |
| 6 | 0.3 | 0.2 | 0.3 | 0.4 | 0.3 | 0.4 | 0.3 | 0.3 |
| 7 | 0.2 | 0.2 | 0.2 | 0.3 | 0.2 | 0.2 | 0.1 | 0.0 |
| 8 | 0.1 | 0.3 | 0.3 | 0.4 | 0.3 | 0.4 | 0.2 | 0.3 |
| Average ± SE = by t Test | 0.27 ± 0.02 P < 0.01 | | 0.31 ± 0.02 P < 0.001 | | 0.33 ± 0.02 P < 0.001 | | 0.21 ± 0.02 P < 0.02 | |
| Isoprinosine 1 | 0.2 | 0.2 | 0.3 | 0.2 | 0.2 | 0.2 | 0.1 | 0.1 |
| 2 | 0.2 | 0.3 | 0.2 | 0.2 | 0.2 | 0.3 | 0.1 | 0.2 |
| 3 | 0.2 | 0.1 | 0.3 | 0.1 | 0.3 | 0.1 | 0.2 | 0.0 |
| 4 | 0.1 | 0.3 | 0.1 | 0.2 | 0.1 | 0.2 | 0.1 | 0.2 |
| 5 | 0.3 | 0.2 | 0.4 | 0.2 | 0.4 | 0.3 | 0.4 | 0.2 |
| 6 | 0.3 | 0.1 | 0.3 | 0.2 | 0.5 | 0.1 | 0.2 | 0.0 |
| 7 | 0.2 | 0.2 | 0.1 | 0.3 | 0.1 | 0.2 | 0.0 | 0.2 |
| 8 | 0.2 | 0.2 | 0.1 | 0.3 | 0.2 | 0.2 | 0.2 | 0.1 |
| Average ± SE = by t Test | 0.21 ± 0.02 P < 0.001 | | 0.22 ± 0.02 P < 0.001 | | 0.23 ± 0.03 P < 0.001 | | 0.14 ± 0.03 P < 0.001 | |

That Isoprinosine exerts biologically significant anti-inflammatory effects on both immunological and non-specific inflammation as pointed out supra is also shown by the following experiments.

EXAMPLE 5

The three new carrageenan studies summarized in this example were carried out using methods identical to those employed in the carrageenan studies in Example 3. In the data presentation that follows, where only the 3-hour time point is given, it is representative.

Study 1

This study establishes that, while Isoprinosine exerts very significant anti-inflammatory effects in the carra-

Study 2

In the disclosure of Example 4, there is reported a two-point dose response curve for Isoprinosine's anti-inflammatory action in carrageenan edema. The animals used in that study had been shipped to applicant's laboratory on the day preceding their use. Since applicant has found certain parameters of drug response to shift as animals habituate to new housing conditions, another dose reponse study was carried out on additional animals from the same shipment one week later. These results identify an anti-inflammatory response plateau that lies between 50 and 200 mg/kg, with the maximum response locating at the low dose end.

| | Footpad Swelling (mm) at 3-hr Post-Carrageenan | % Drug Effect |
|---|---|---|
| Control | 0.36 ± 0.03 | |
| Isoprinosine 50 mg/kg | 0.27 ± 0.03* | 25% |
| Isoprinosine 100 mg/kg | 0.28 ± 0.02* | 22% |
| Isoprinosine 200 mg/kg | 0.27 ± 0.03* | 25% |

*$P < 0.05$

Study 3

This study compares effects of Isoprinosine, Indomethacin, and Prednisone on carrageenan edema in the standard system described in the preceding example. Drug comparison across the 3-hour response point revealed similar anti-inflammatory effects for all the compounds; however, when effects across 1-, 2-, and 3-hours post-carrageenan are summed and compared, then Prednisone and 100 mg/kg Isoprinosine emerge as the more effective drugs. In this study, both 500 mg/kg Isoprinosine and Indomethacin are observed to exert an early suggestion of a pro-inflammatory effect. A transient pro-inflammatory effect for Indomethacin has been observed by applicant in other carrageenan systems and, interestingly, has been reported clinically as an occasional response observed at the onset of treatment.

The possible significance of this dose effect is that, in studies of Isoprinosine in human inflammatory disease, a specific change in regimen for an individual non-responder patient may be to lower the drug dose.

| | Footpad Swelling (mm) | | | Sum |
|---|---|---|---|---|
| | 1 Hour | 2 Hours | 3 Hours | Hours 1-3 |
| Control Isoprinosine | 0.29 ± 0.03 | 0.47 ± 0.03 | 0.51 ± 0.02 | 1.26 ± 0.06 |
| 100 mg/kg | 0.26 ± 0.03 | 0.39 ± 0.03$^c$ | 0.36 ± 0.02$^a$ | 1.01 ± 0.07$^b$ |
| Drug effect | 10% | 17% | 29% | 20% |
| 500 mg/kg | 0.39 ± 0.04$^c$ | 0.46 ± 0.04 | 0.32 ± 0.03$^a$ | 1.18 ± 0.09 |
| Drug effect | −34% | 2% | 37% | 6% |
| Indomethacin* | 0.36 ± 0.03 | 0.39 ± 0.04 | 0.34 ± 0.03$^a$ | 1.09 ± 0.09 |
| Drug effect | −24% | 17% | 33% | 13% |
| Prednisone** | 0.29 ± 0.03 | 0.26 ± 0.03$^a$ | 0.24 ± 0.04$^a$ | 0.79 ± 0.08$^a$ |
| Drug effect | 0% | 45% | 53% | 37% |

*Indomethacin dose - 5mg/kg;
**Prednisone dose - 2.5 mg/kg
$^a$P $< 0.001$;
$^b$P $< 0.02$;
$^c$P $< 0.05$ Following the intra-footpad injection of 500-100 μg lambda carrageenan for each 20 grams of body weight in either mouse or rat, footpad swelling develops progressively over several hours, typically peaking in the neighborhood of 3 hours in the mouse and 4 hours in the rat. The early swelling, as a 1 hour, is due largely to the local release of biogenic amines and bradykinin. It consists principally of a fluid influx resulting from increased vascular permeability. After 2 hours, inflammatory components come principally from the influx of monocytes and the release of lysosomal enzymes, tissue-damaging active oxygens and pro-inflammatory prostaglandins from this cellular infiltrate. Pharmaceutical laboratories concerned with screening anti-inflammatory compounds frequently use the 3-hour post-carrageenan time period as a single time point at which drug actions are assessed and compared. This is the established 3-hour "window" through which one can observe therapeutically useful anti-inflammatory drug effects.

EXAMPLE 6

ISOPRINOSINE SUPPRESSION OF CARRAGEENAN FOOTPAD EDEMA IN THE RAT

This is an in vivo experiment. Isoprinosine given by oral gavage 2 hours prior to carrageenan injection, total volume 0.5 ml.

There were employed male Sprague-Dawley rats, 180–200 g, 6–7 weeks of age, obtained from Harlan.

The inoculum was 1 mg/paw lambda carrageenan, type IV (Sigma Chemical Col. Lot 190 40F-0388), made up in saline, total volume 0.05 ml.

The method classically used in the pharmaceutical industry for the study of drug effects on carrageenan edema was employed in the study of Isoprinosine: the experimental animal was the laboratory rat and the lambda carrageenan thus employed was 1 mg/paw, which produces a diameter increase at 3 hours of about 100%.

Two hours prior to carrageenan injection, the rats received an oral gavage of 0.5 ml distilled water with or without Isoprinosine. Two hours later, following initial footpad measurements using a Schnelltaster caliper, rats were etherized and injected subcutaneously in each hind footpad with 1 mg carrageenan. Measurements of footpad diameters were carried out at 3 hours, and paw swellings were determined.

Part A consisted of two groups of rats: Control and Isoprinosine, 6 rats/group, N=12 paws. Isoprinosine was given at 150 mg/kg.

Part B consisted of four groups of 5 rats, N=10 paws, as follows:
Control
Isoprinosine, 15 mg/kg
Isoprinosine, 50 mg/kg
Isoprinosine, 150 mg/kg
Part A—Increase in control footpad diameter at 3 hours was 96.7%.

| | Footpad Swelling at 3 Hours | | |
|---|---|---|---|
| | mm | % DE* | by t Test |
| Control | 3.53 ± 0.12 | | |
| Isoprinosine | 1.82 ± 0.24 | 48.4% | P < 0.001 |

*Drug effect

Part B—Increase in control footpad diameter at 3 hours was 104%.

| | Footpad Swelling at 3 Hours | | |
|---|---|---|---|
| | mm | % DE | by t Test |
| Control | 3.93 ± 0.16 | | |
| Isoprinosine, 15 | 3.35 ± 0.19 | 14.8% | P < 0.05 |
| Isoprinosine, 50 | 3.16 ± 0.12 | 19.6% | P < 0.001 |
| Isoprinosine, 150 | 2.56 ± 0.26 | 34.9% | P < 0.001 |

These results show that Isoprinosine suppresses carrageenan footpad edema in the rat and that this effect is dose dependent between 15 and 150 mg/kg.

These data establish the anti-inflammatory effectiveness of Isoprinosine in a second species, the rat, which is the animal typically used by the industry in screening for anti-inflammatory action via the carrageenan footpad edema model.

The depression in swelling of between 35% and 48% is an excellent drug effect in comparison with that generated by the industry standard, indomethacin. Thus, C. A. Winter of Merck Institute for Therapeutic Research finds indomethacin to suppress carrageenan footpad edema by 32% at 1 mg/kg 40% at 3 mg/kg, and 50% at about 8 mg/kg (in *Non-Steroidal Anti-Inflammatory Drugs*, Excerpta Medical Foundation, New York, 1965, pp. 190-202). Three mg/kg of indomethacin is the maximum total daily dosage of this anti-inflammatory drug that is ever given to humans.

EXAMPLE 7

ISOPRINOSINE SUPPRESSION OF KAOLIN FOOTPAD EDEMA IN THE RAT

This is an in vivo experiment. Isoprinosine, 150 mg/kg, given by oral gavage 2 hours prior to kaolin injection, total volume 0.5 ml.

Male Sprague-Dawley rats, 200 g, 6½ weeks of age, obtained from Harlan, 6 rats/group (N=12 paws).

The inoculum was 10 mg/paw kaolin (hydrated aluminum silicate; Sigma Chemical Co. Lot 190 101F-0412), made up in saline, total volume 0.1 ml.

Kaolin (hydrated aluminum silicate) is frequently used in the pharmaceutical industry to demonstrate the broad spectrum nature of non-specific anti-inflammatory drug effects.

Two hours prior to kaolin injection, rats received an oral gavage of 0.5 ml distilled water with or without Isoprinosine (150 mg/kg). Two hours later, following initial footpad measurements using a Schnelltaster caliper, rats were etherized and injected subcutaneously in each hind footpad with 10 mg kaolin. Measurements of footpad diameters in this slowly developing inflammation were carried out at 7 hours, as recommended (Wong, S., J. F. Gardocki, and T. P. Pruss, *J. Pharmacol. Exp. Therap.* 185, 127–138, 1973).

Increase in control footpad diameter at 7 hours was 75.5%.

| | Footpad Swelling at 7 Hours | | |
|---|---|---|---|
| | mm | % Drug Effect | t Test Statistics |
| Control | 2.78 ± 0.18 | | |
| Isoprinosine | 2.18 ± 0.15 | 21.6% | P < 0.02 |

These results illustrate that Isoprinosine can suppress kaolin footpad edema in the rat.

These data confirm that Isoprinosine possesses a broad spectrum anti-inflammatory action that can operate independent of immune mechanisms.

As regards the modest nature of the drug effect at the dose studied, it should be noted that kaolin edema is typically more resistant than carrageenin edema to anti-inflammatory action (Garattini, S., et al, p. 151 in *International Symposium on Non-Steroidal Anti-Inflammatory Drugs*, S. Garattini and M. Dukes eds., Exerpta Medica Foundation, Amsterdam, 1965).

EXAMPLE 8

ISOPRINOSINE INTERACTION WITH INDOMETHACIN AND SODIUM SALICYLATE, TWO ESTABLISHED NON-STEROIDAL ANTI-INFLAMMATORY DRUGS

In a study of the treatment of human arthritis as set forth above, Wybran and Appelboom have reported that the addition of Isoprinosine to a regimen of indomethacin or acetylsalicylic acid (aspirin) intensified anti-arthritic effects in 9/15 cases; in 2/15 cases, addition of Isoprinosine made the inflammatory condition worse. It is significant that the Wybran and Appelboom study did not examine Isoprinosine alone for its effects on this inflammatory condition, but rather examined Isoprinosine only in combination with known non-steroidal anti-inflammatory drugs (NSAID).

The potential for significant drug interaction renders the Wybran and Appelboom data difficult to interpret. These questions come to mind:

Did Isoprinosine act through a prolongation of the half-life or potentiation of the pharmacological activity of the other drugs?

Did Isoprinosine, in some individuals, exert an antagonism to the effects of the anti-inflammatory treatments?

In the present studies, experimental inflammation was produced in mice by the means described in the previous example. Immunization was by human serum albinim (HSA) in complete Freund's adjuvant (CFA) per hind paw footpad and antigen challenge enhancing or producing the inflammation was by administration of HSA orally or by footpad injection, as noted, between days 22–43 following immunization. Four separate studies were carried out, employing 14–16 paws per treatment group. In this example, the drugs were fed orally. The dosages employed were as follows:

Isoprinosine: 100 mg/kg
Indomethacin: 2 mg/kg
Indomethacin: 2 mg/kg with Isoprinosine: 100 mg/kg
Sodium salicylate: 300 mg/kg
Sodium salicylate: 300 mg/kg with Isoprinosine: 100 mg/kg.

The results shown in FIGS. 6–9 confirm applicant's observation that Isoprinosine can inhibit inflammation in mammals and depict the mutual interference that occurs between Isoprinosine, on the one hand, and indomethacin and sodium salicylate, on the other, when Isoprinosine is used in combination with either of the other drugs.

The previous examples have established that Isoprinosine can exert broad-spectrum anti-inflammatory effects. In the studies discussed in this example, it is shown that Isoprinosine and NSAID can significantly inhibit each other's anti-inflammatory actions. Combining drugs can, in fact, result in a significantly poorer anti-inflammatory effect than using Isoprinosine or the other drug alone.

It is possible that this "negative" interaction derives from the fact that, while NSAID inhibit the synthesis of all pro- and anti-inflammatory prostaglandins, Isoprinosine strikingly potentiates the anti-inflammatory actions of the anti-inflammatory prostaglandin, $PGE_1$. In any event, this kind of interaction may have contributed to the results of Wybran and Appelboom.

The inosiplex of the invention can be used to treat inflammatory diseases having a non-specific component, e.g., rheumatoid arthritis, in mammals such as humans, monkeys, cats, dogs, rats, mice, horses, cattle, sheep, and pigs.

In addition the inosiplex of the invention can be used to treat the inflammatory disease Lupus Erythematosis, having a non-specific component.

The compositions employed can comprise, consist essentially of, or consist of inosiplex. The inosiplex is usually employed in a pharmaceutically acceptable carrier, e.g., water, or as a tablet or capsule with appropriate pharmaceutical carriers.

The inosiplex can be administered orally, paranterally, in interparenterally, or by other means.

What is claimed is:

1. A method of treating an inflammatory disease having a non-specific component comprising administering to a mammal afflicted with such disease an amount of inosiplex effective to reduce the inflammation, the inosiplex being administered in the absence of indomethacin or aspirin.

2. A method according to claim 1 wherein the inflammatory disease is rheumatoid arthritis.

3. A method of treating an inflammatory disease having a non-specific component comprising administering to a mammal afflicted with such disease an amount of inosiplex effective to reduce the inflammation, the inosiplex being administered in the absence of any other non-steroid anti-inflammatory drug.

4. A method according to claim 3 wherein the inflammatory disease is rheumatoid arthritis.

5. A method according to claim 2 wherein inosiplex is the sole drug administered.

6. A method according to claim 3 wherein inosiplex is the sole drug administered.

7. A method according to claim 6 wherein there is employed 15 to 500 mg/kg body weight of the inosiplex.

8. A method according to claim 5 wherein there is employed 15 to 500 mg/kg body weight of the inosiplex.

9. A method according to claim 2 wherein the inosiplex is administered orally.

10. A method according to claim 1 wherein the inosiplex is administered orally.

* * * * *

UNITED STATES PATENT AND TRADEMARK OFFICE
CERTIFICATE OF CORRECTION

PATENT NO. : 4,512,981

DATED : April 23, 1985

INVENTOR(S) : Paul Gordon

It is certified that error appears in the above-identified patent and that said Letters Patent is hereby corrected as shown below:

Column 6 of Table 3 at "Day 4,L", "0.1" should be -- -0.1 --;

Column 7 of Table 3 at "Day 3,L", "0.0" should be --  0.2 --;

Column 12, line 22, "(Sigma Chemical Col. Lot 190 40F-0388)" should be --(Sigma Chemical Co. Lot #40F-0388)--;

Column 13, line 51, "Lot 190 101F-0412)" should be --Lot # 101F-0412--.

Signed and Sealed this

Twelfth Day of August 1986

[SEAL]

Attest:

DONALD J. QUIGG

Attesting Officer

Commissioner of Patents and Trademarks